US009110016B2

(12) United States Patent
Chartier et al.

(10) Patent No.: US 9,110,016 B2
(45) Date of Patent: Aug. 18, 2015

(54) METHOD FOR ISOTOPIC MEASUREMENT BY ICPMS (75) Inventors: Frédéric Chartier, Fontenay-aux-Roses (FR); Valérie Geersten, Versailles (FR); Laurent Vio, Dagneux (FR); Gérard Crétier, Dagneux (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 13/991,295

(22) PCT Filed: Dec. 2, 2011

(86) PCT No.: PCT/FR2011/052848
§ 371 (c)(1),
(2), (4) Date: Jun. 3, 2013

(87) PCT Pub. No.: WO2012/072963
PCT Pub. Date: Jun. 7, 2012

(65) Prior Publication Data
US 2013/0248365 A1 Sep. 26, 2013

(30) Foreign Application Priority Data

Dec. 3, 2010 (FR) ...................................... 10 60049

(51) Int. Cl.
*G01N 27/447* (2006.01)
*H01J 49/10* (2006.01)
(Continued)

(52) U.S. Cl.
CPC .......... *G01N 27/44721* (2013.01); *B01D 59/42* (2013.01); *G01N 27/447* (2013.01);
(Continued)

(58) Field of Classification Search
CPC ...................... G01N 27/447; G01N 27/44756
USPC ................................................... 204/645, 549
See application file for complete search history.

(56) References Cited

U.S. PATENT DOCUMENTS 4,885,076 A * 12/1989 Smith et al. ................... 204/451
RE34,757 E * 10/1994 Smith et al. ................... 204/452
(Continued)

OTHER PUBLICATIONS

Viczian et al. (J. Anal. At. Spec., Jun. 1990, vol. 5, 293-300).*
(Continued)

*Primary Examiner* — Luan Van
*Assistant Examiner* — Steven Rosenwald
(74) *Attorney, Agent, or Firm* — Browdy and Neimark, PLLC (57) ABSTRACT A method for isotope measurement of charged species contained in a solution to be analyzed, particularly charged species having an isobaric interference, has the following consecutive steps:
  a) in the capillary of a capillary electrophoresis device, the solution to be analyzed is inserted contiguously between a terminating electrolyte and a leading electrolyte that, respectively, are placed after the inlet and before the outlet of the capillary and contain ions of the same charge but with mobility inferior and superior to those of said species;
  b) separating the species by using the capillary electrophoresis device according to the isotachophoresis mode; then
  c) in the continuity of the preceding step, performing an isotope measurement of the species detected in the form of a substantially constant amplitude signal by using an inductively coupled plasma mass spectrometer (ICPMS) connected by direct coupling with the capillary electrophoresis device.

18 Claims, 3 Drawing Sheets (51) Int. Cl.
*B01D 59/42* (2006.01)
*B01D 59/44* (2006.01)
*G01N 30/88* (2006.01)

(52) U.S. Cl.
CPC .... *G01N27/44717* (2013.01); *G01N 27/44756* (2013.01); *H01J 49/105* (2013.01); *B01D 59/44* (2013.01); *G01N 2030/8868* (2013.01)

(56) References Cited

U.S. PATENT DOCUMENTS 6,610,978 B2 * 8/2003 Yin et al. .................. 250/288
2002/0139931 A1 * 10/2002 Yin et al. .................. 250/288

OTHER PUBLICATIONS

Mao et al. (J. Chrom. A, 802, 1998, 203-210).*
Taylor et al. (J. Anal. At. Spectrom., 2001, 16, 279-284).*
Day et al. (J. Anal. At. Spectrom., 2000, 15, 1343-1348).*
Goutelard et al. (High precision and accurate isotopic and elemental analysis of spent nuclear fuels: new trends in separation techniques in Nuclear fuel cycle and fuel materials 41/;47, pp. 170-177.*
Viczian et al. (J. Anal. At. Spectrom., 1990, 5, 125).*
Barnes, R. M., "Capillary Electrophoresis and Inductively Coupled Plasma Spectrometry: Status Report", Fresenius Journal of Analytical Chemistry, vol. 361, No. 3, pp. 246-251, Jun. 1998
Michalke, B., "Capillary Electrophoresis-Inductively Coupled Plasma Spectrometry: A Report on Technical Principles and Problem Solutions, Potential, and Limitations of This Technology as well as on Examples of Application", Electrophoresis, vol. 26, No. 7-8, pp. 1584-1597, Apr. 2005.
Hirokawa et al., "Preparative procedures in isotachophoresis", Journal of Chromatography, vol. 658, No. 2, pp. 343-354, Jan. 1994
Mazereeuw, M. et al., "In-line isotachophoretic focusing of very large injection volumes for capillary zone electrophoresis using a hydrodynamic counterflow", Journal of Chromatography, vol. 677, No. 1, pp. 151-157, Aug. 1994.
Qi Jun Song et al., "Interfacing a microfluidic electrophoresis chip with inductively coupled plasma mass spectrometry for rapid elemental speciation", Journal of Analytic Atomic Spectrometry, vol. 19, No. 7, pp. 883-887, Jun. 2004.
Pitois et al., "Determination of fission products in nuclear samples by capillary electrophoresis-inductively coupled plasma mass spectrometry (CE-ICP-MS)", International Journal of Mass Spectrometry, vol. 270, No. 3, pp. 118-126, Dec. 2007.
Ignacio, Garcia Alonso et al., "Determination of fission products and actinides in spent nuclear fuels by isotope dilution ion chromatography inductively coupled plasma mass spectrometry", Journal of Analytic Atomic Spectrometry, vol. 10, No. 5, pp. 381-393, May 1995.
Mazereeuw M. et al., "On-line isotachophoretic sample focusing for loadability enhancement in capillary electrochromatography-mass spectrometry", Journal of Chromatography, vol. 879, No. 2, pp. 219-233, May 2000.
Udseth, H. R. et al., "Capillary Isotachophoresis/Mass Spectrometry", Analytical Chemistry, vol. 61, No. 3, pp. 228-232, Feb. 1989.
G. V. Kaigala et al., "Miniaturized System for isotachophoresis assays", Lab Chip, vol. 10, No. 17, p. 2242, Jan. 2010.
Petit, J. et al., "Metal complexes stability constant determination by hyphenation of capillary electrophoresis with inductively coupled plasma mass spectrometry: The case of 1:1 metal-to-ligand stoichiometry", Journal of Chromatography, vol. 1216, No. 18, pp. 4113-4120, May 2009.

* cited by examiner

METHOD FOR ISOTOPIC MEASUREMENT BY ICPMS

TECHNICAL FIELD

This invention relates to the field of methods for qualitative or quantitative analysis of constituents of a sample using an inductively coupled plasma mass spectrometer (abbreviated as "ICPMS").

The invention relates more specifically to a method for isotope measurement by ICPMS spectrometry of electrically charged species, in particular inorganic or organometallic species, contained in a solution to be analyzed.

TECHNICAL BACKGROUND

The isotope measurement consists of determining the presence and/or concentration in a sample of one or more isotopes of a chemical element.

It is performed in particular in the nuclear, life science (bioavailability, speciation studies, etc.), environmental and earth science (determination of isotope variation, speciation and migration-retention of elements, etc.) fields.

The isotope measurement is commonly performed using an ICPMS spectrometer.

This type of spectrometer consists of a plasma torch and a mass spectrometer.

The plasma torch contains a gas that, under the action of an electrical discharge and a radiofrequency field, generates a plasma that ionizes, with close to 100% efficiency, all or some of the elements introduced into to the torch in elemental or compound form.

The ions thus formed are then analyzed by the mass spectrometer portion that detects each ion according to its mass-to-charge ratio.

ICPMS spectrometry has been an indispensable analysis technique for many years. It makes it possible to quickly analyze, qualitatively and quantitatively, at least 70 elements of the periodic table, with good repeatability, sensitivity, resolution and a linear relationship between the quantity of species to be analyzed and the signal detected.

When the solution to be analyzed comprises multiple charged species, it is, however, preferable to improve the resolution of the measurement by first separating the species with a separation technique such as chromatography or capillary zone electrophoresis.

This separation upstream of the measurement is essential in particular when the solution to be analyzed contains species having an isobaric interference due to their adjacent mass. This is the case, for example, of elements $^{150}$Nd and $^{150}$Sm, with respective atomic masses of 149.920887 and 149.917271 atomic mass units (u).

In practice, the separation technique can be associated with the ICPMS spectrometer by an indirect (or off-line) coupling or by a direct (or on-line) coupling mode.

In indirect coupling, the isotope measurement is performed in two stages. In a first stage, the species contained in the solution to be analyzed are separated, and then collected individually at the outlet of the separation technique. In a second stage, each collected fraction is dried by heating, nitric acid is added, and then the collected fraction is analyzed by the ICPMS spectrometer.

Each fraction contains a single species. It therefore has a homogeneous composition. The signal measured by the ICPMS spectrometer is then continuous, which has the advantage of ensuring the stability and therefore the precision of the measurement.

Indirect coupling nevertheless has the disadvantage of requiring fraction collection and treatment steps, which are difficult to automate, and which significantly prolong the overall time of the analysis process.

In direct coupling, the isotope measurement is performed in a single sequence. Once separated, the species are introduced continuously into the ICPMS spectrometer coupled to the separation technique via a suitable interface. The direct coupling therefore eliminates the collected fraction treatment inherent to indirect coupling, and thereby notably reduces the measurement time. The document "Pitois A. et al, international Journal Of Mass Spectrometry, 2008, 270, pages 118-126" thus proposes an isotope measurement in which nuclear fission products are separated by zone electrophoresis using a capillary electrophoresis device connected by direct coupling to an ICPMS spectrometer.

Direct coupling nevertheless has a disadvantage in that the composition varies over time as the elution zone specific to each separated species reaches the outlet of the separation technique. This causes a significant and rapid variation in the signal between the measurement points. This transient signal is den recorded by the ICPMS spectrometer with a precision and reproducibility inferior to that of indirect coupling.

Moreover, it appears to be difficult to estimate the extent of the elution zone over which it is desirable to perform the recording by the ICPMS spectrometer, which is detrimental to the representativeness of the measurement. Thus, the reproducibility in direct coupling is generally ten times worse than that obtained in indirect coupling.

DESCRIPTION OF THE INVENTION

One of the objectives of the invention is therefore to provide a method for isotope measurement of charged species, in which the coupling between the reparative technique and the ICPMS spectrometer has all or some of the aforementioned advantages of direct and indirect coupling. Such a method in particular enables an automatable measurement that takes less time, and has improved reproducibility and resolution, in particular when the solution to be analyzed has an isobaric interference.

This invention thus relates to a method for isotope measurement of charged species contained in a solution to be analyzed, the method comprising the following consecutive steps:

a) in the capillary of a capillary electrophoresis device, inserting contiguously the solution to be analyzed between a terminating electrolyte and a leading electrolyte that, respectively, are placed after the inlet and before the outlet of the capillary and contain ions of the same charge but with mobility inferior and superior to those of the species;

b) separating the species by using the capillary electrophoresis device according to the isotachophoresis mode, then;

c) in the continuity of the preceding step, performing an isotope measurement of the species detected in the form of a substantially constant amplitude signal by using an inductively coupled plasma mass spectrometer (ICPMS) connected by direct coupling with the capillary electrophoresis device.

The measurement method of the invention is characterized among others by the use of isotachophoresis, which is a particular embodiment of a capillary electrophoresis device, as well as by the fact that the ICPMS spectrometer is connected by direct coupling with the capillary electrophoresis device, which makes it possible to perform the isotope measurement according to step c) in the continuity of the separation according to step b). As described below, only the combination of these two features makes it possible to achieve the objectives of the invention.

A capillary electrophoresis device consists essentially of two containers connected by a capillary column (hereinafter referred to as "capillary"), each container containing an electrolyte and an electrode. After applying a voltage between the two electrodes, the charged species to be analyzed introduced into the capillary filled with electrolyte separate according to their effective electrophoretic mobility (called mobility), which is dependent on their (electrical charge)/(size) ratio. The separated species are then detected by means of a suitable analysis technique.

The isotachophoresis mode of capillary electrophoresis is characterized by the use of a discontinuous separation medium consisting of a leading electrolyte and a terminating electrolyte with a distinct composition, between which the solution to be analyzed is contiguously inserted. The leading and terminating electrolytes are respectively placed after the inlet and before the outlet of the capillary, and have an effective mobility superior and inferior to those of the species to be analyzed. The composition of the electrolytes must therefore take into account the value of the effective mobilities of the species to be analyzed, to ensure that these species are separated.

After applying a voltage between the electrodes, the species will be progressively ordered according to increasing mobility until a state of equilibrium. They are then distributed into clearly defined contiguous elution zones specific to them, at a homogeneous concentration equal to that of the leading electrolyte. The species are therefore concentrated or diluted according to their initial concentration in the solution to be analyzed. This is why isotachophoresis is generally essentially used for pre-concentrating the species and not for separating them.

Isotachophoresis is therefore distinguished from the conventional implementation of capillary electrophoresis (capillary zone electrophoresis or free solution capillary electrophoresis) by the use of a discontinuous separation medium (at least two electrolytes instead of just one), but also by the fact that, since the concentration of a species to be analyzed is homogeneous at all points of the elution zone obtained in isotachophoress, its detection results in a constant or substantially constant amplitude signal in this zone, rather than a peak reflecting a variation in concentration over time. Such a signal (for example, a band) therefore generally has amplitude variations of less than 25% (preferably 10% to 15%) of its mean amplitude over 50% (preferably 80%) of its median width.

The number of measurement points that can be recorded by the ICPMS spectrometer is dependent on the width of the elution zone.

This is one of the major disadvantages of a conventional separation by capillary zone electrophoresis, which, when it is effective, generates narrow elution peaks of maximum amplitude, and therefore of minimal duration, offering a small number of measurement points per unit of time. There is therefore a high variation in amplitude of the transient signal between two consecutive points causing instability and imprecision of the ICPMS spectrometer measurement.

By contrast, according to the isotope measurement method of the invention, the separation by isotachophoresis of the charged species results in their detection in the form a transient signal of constant amplitude and significant duration (generally a signal in the form of a band), which no other separation technique, such as chromatography or capillary zone electrophoresis makes it possible to obtain.

As shown below for the calculation of the resolution (Rs), this special feature of isotachophoresis facilitates and rationalizes the treatment of the signal and makes it possible to obtain a measurement by ICPMS that is more stable and more precise by comparison with that obtained with a signal in the form of a peak.

This separation of species with the capillary electrophoresis device according to the isotachophoresis mode should be distinguished from separation in which the species are subjected, in a first stage, to isotachophoresis ("ITP") in order to pre-concentrate them, then separated in a second stage by a conventional separation mode by capillary electrophoresis ("CE"), this mode being referred to as "ITP-CE", that is, ITP followed by CE.

The use of separation by capillary electrophoresis according to a mode other than isotachophoresis (such as, for example, capillary zone electrophoresis, or "CZE") does not in any case enable charged species to be detected in the form of a signal of constant or substantially constant amplitude, and therefore the aforementioned advantages of the measurement method of the invention to be obtained.

To this end, it should be noted that only direct coupling between the ICPMS spectrometer and the capillary electrophoresis device makes it possible to perform step c) in the continuity of step b) of the measurement method of the invention, and thus to preserve, in the isotope measurement using the ICPMS spectrometer, a signal of constant or substantially constant amplitude previously obtained by isotachophoresis.

It is therefore the combination of the separation of species by isotachophoresis and their detection using a spectrometer (ICPMS) connected by direct coupling with the capillary electrophoresis device that makes it possible to obtain the advantages of the measurement method of the invention.

Such advantages can even be enhanced by increasing the width in the elution zone (and therefore the duration of the transient signal, for example, in the form of a band) by reducing the intensity of the current applied in the separation, which, in isotachophoresis, does not affect the efficacy of the separation.

Preferentially, it is thus possible to separate the charged species by applying a low current intensity when implementing the isotachophoresis step of the measurement method of the invention, i.e. preferably an intensity between 0.1 µA and 10 µA, even more preferably between 1 µA and 10 µA, and even between 1 µA and 5 µA.

In spite of the long existence of the isotachophoresis and ICPMS techniques, the inventors are, to their knowledge, the first to have identified the benefit of combining these techniques by direct coupling, in order to perform the isotope measurement of charged species, obtaining all or some of the advantages of direct coupling and indirect coupling.

DETAILED DESCRIPTION OF THE INVENTION

In the present description, a verb such as "comprise", "incorporate", "include" and its conjugated forms are open terms and do not therefore rule out the presence of additional elements and/or steps in addition to the initial element(s) and/or step(s) indicated after these terms. However, these open terms also relate to a specific embodiment in which only the initial element(s) and/or step(s), excluding any other, are covered; in this case, the open term also refers to the closed term "consist of", "constituted by" and its conjugated forms.

The use of the indefinite article "a" or "an" for an element or a step does not rule out, unless otherwise indicated, the presence of multiple elements or steps.

The isotope measurement performed using the method of the invention can be quantitative or qualitative.

In this description, it consists among others in determining for at least one isotope of charged species to be analyzed:
the presence or absence of the isotope;
the isotopic abundances of the different isotopes of the same species;
the concentration in solution of the isotope by an isotope dilution technique as described, in the document. "Méthodes d'analyses radiochimdques isotopiques [Radiochemical and isotope analysis methods], G. Revel, Techniques de l'Ingénieur, issue P2595)". The isotope dilution comprises, in particular:
single isotope dilution (direct): this consists of adding a tracer of known concentration consisting of the same species but of different isotopic composition, for example enriched with one of its isotopes. This method makes it possible to perform high-precision measurements, without a calibration line and measuring only isotope ratios;
double isotope dilution: the ratio of abundance between two isotopes of distinct species (such as $^{145}$Nd/$^{235}$U) is determined by adding a double isotope tracer.

When the isotope measurement according to the method of the invention consists of a quantitative analysis, it preferably comprises an isotope dilution, preferably a single or a double isotope dilution, or the precise measurement of the relative abundances of the isotopes of a species.

The charged species are cations or anions that, during the isotachophoresis, migrate respectively toward the cathode or the anode. They can in particular comprise inorganic cations (among others, transition, alkaline or alkaline earth metals), inorganic anions, organometallic compounds or mixtures thereof.

When the charged species to be analyzed are compounds, the isotope considered is the isotope of an element contained in these compounds.

Owing to its advantages, in particular its improved resolution, the measurement method of the invention is particularly beneficial when at least two of the charged species have at least one isobaric interference, preferably when this interference is such that the difference in atomic mass between the species is between 0.001 and 0.9 atomic mass units (u). The measurement method of the invention is thus particularly suitable for the analysis of a solution comprising lanthanides and/or actinides, these species frequently having at least one isobaric interference.

The leading or terminating electrolyte used during she isotachophoresis generally has a concentration of between 1 mM and 100 mM, preferably between 10 mM and 20 mM.

It usually usually has a buffer capacity. The terminating electrolyte can thus be a zwitterionic compound (carnitine chloride, β-alanine, etc.), in particular a carboxylic acid (preferably acetic acid).

The pH of the electrolytes is generally between 3.5 and 5.2, after a possible adjustment using, for example, ammoniac or acetic acid according to the required pH conditions.

Preferably, the leading and/or terminating electrolyte is an aqueous solution of a compound comprising the elements carbon, hydrogen and oxygen (and possibly nitrogen).

This enables easy destruction of the electrolytes after implementation of the measurement method of the invention, as well as total compatibility with the ICPMS detection (no contamination of the ICPMS spectrometer with atoms such as Na, Li, K or P possibly present in a high concentration).

To improve she separation of she charged species, the capillary may also contain a complexing agent intended to form at least one complex with all or some of the charged species during the isotachophoresis. This is particularly useful when these species comprise a plurality of lanthanides, because, as their mobilities are generally similar, they are separated according to the stability of the complex formed.

This improvement in the separation can be further reinforced by adding an assisting agent to the complexing agent (called the synergy agent) in order to form at least one mixed complex with all or some of the charged species.

The complexing agent and/or the assisting agent is preferably contained in the leading electrolyte.

Depending on the species to be separated, the complexing agent may be chosen from 2-hydroxy-2-methyl butyric acid (HMEA) (preferably, in particular when the species comprise lanthanides and/or actinides), hydroxyisobutyric acid (HIBA), ethylenediaminetetraacetic acid (EDTA), pyridine-2,6-dicarboxylic acid (PDCA), lactic acid, tartric acid, oxalic acid, malonic acid, maleic acid, isobutyric acid or mixtures thereof.

The assisting agent may be chosen from diglycolic acid, malonic acid, maleic acid, formic acid, citric acid, acetic acid, tartric acid (preferably), or mixtures thereof.

Even more preferably, when the charged species to be analyzed contain the elements Eu and Gd, the complexing agent is HIBA or EDTA, associated with tartric acid (preferably) or maionic acid.

Concerning the equipment used by the measurement method of the invention, the capillary electrophoresis device may be entirely or partially implanted on a fluidic mdcrosystem, of which it preferably constitutes the injection system. Such an embodiment enables an isotope measurement of a solution to be analyzed having a low volume, as well as the implementation of a disposable system, eliminating washing and cross-contamination between different isotope measurements.

The material constituting the portion of the fluidic microsystem in contact with the solution to be analyzed is preferably comprised of a plastic material chosen from a cyclic olefin copolymer (CoC), polydimethylsiloxane (PDMS) or poly(methyl methacrylate) (PMMA).

Among these compounds, CoC is preferably used owing to its low cost, its good mechanical properties which make it suitable for the techniques of machining and manufacturing of a fluidic microsystem by hot embossing, its electrical properties, which enable it to resist high electrical fields, as well as its chemical inertia and its hydrophobicity, which make it compatible with numerous solvents, without fear of modifying its surface properties in the isotope measurement.

The CoC is, for example, Zeonor 1020R (marketed by the ZEONEX company).

Concerning the ICPMS spectrometer, any type suitable for the isotope measurement of charged species may be used.

It may be, for example, a quadripolar, magnetic sector time-of-flight (ICP-TOF) ICPMS spectrometer it may be of the single-collection or the multi-collection type.

Preferably, the ICPMS spectrometer is of the multi-collection type, that is, it has a plurality of detectors on the trajectory of the deflected ions, which makes it possible to simultaneously acquire a plurality of signals each corresponding to a given mass, and therefore to a given charged species. This type of spectrometer makes it possible to perform an isotope measurement with improved precision, accuracy and speed, on a wide range of chemical elements and at very low concentrations. This promotes the implementation of isotope measurements using a plurality of isotope tracers, such as double isotope dilution.

To best compensate for the difference in flow rate between the outlet of the capillary and the inlet of the ICPMS spectrometer while closing the electrical circuit at the outlet of the capillary, the capillary electrophoresis device and the ICPMS spectrometer are connected by direct coupling, preferably via a system enabling drops to be generated, such as, for example, a piezoelectric drop generator (marketed in particular by the Microdrop company) or a nebulizer. Such a system is described in particular in the document "Michalke B, Electrophoresis, 2005, vol. 26, no 7-8, pages 1584-1597".

Other objectives, features and advantages of the invention will now be specified in the following description of specific embodiments of the measurement method of she invention, provided for illustrative and non-limiting purposes, in reference to the appended FIGS. 1 to 5.

DESCRIPTION OF SPECIFIC EMBODIMENTS

The specific embodiments of the measurement method of the invention relate to the analysis of three lanthanide solutions using equipment consisting of a capillary electrophoresis device (comprising a conductometric sensor) connected by direct coupling, via a nebulizer, to an ICPMS spectrometer.

1. Equipment.

1.1. Capillary Electrophoresis Device.

Unless otherwise specified, the following description of the capillary electrophoresis device and the associated process conditions can be transposed to the specific case in which this device is in the form of a fluidic microsystem.

The capillary electrophoresis device comprises an anode and a cathode, which are comprised of platinum.

Its capillary is placed in a thermostatically-controlled cassette at a temperature of 25° C.

The internal surface of the capillary is lined with a fused silica coating. Alternatively, a coating comprised of Teflon or CCC may also be suitable.

Each of the ends of the capillary is immersed in a container: the inlet of the capillary in the container containing the terminating electrolyte, and the outlet of the capillary in the container containing the leading electrolyte.

The outlet container and its electrode (in this case, the cathode) open into the nebulizer.

Figure 1:
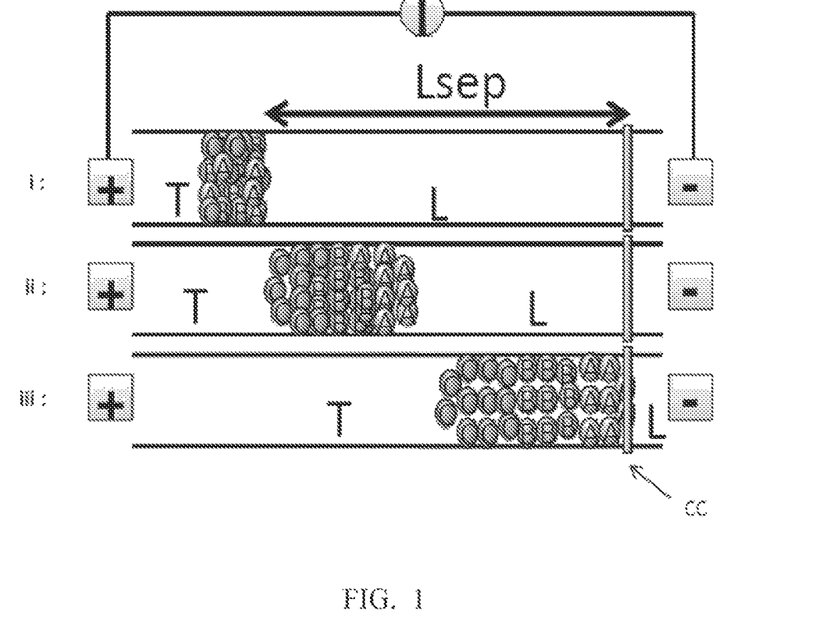
FIGS. 1 and 2 show the principle of the separation of charged species by isotachophoresis and the corresponding isotachopherogram that would be obtained by conductometric detection.
Figure 2:
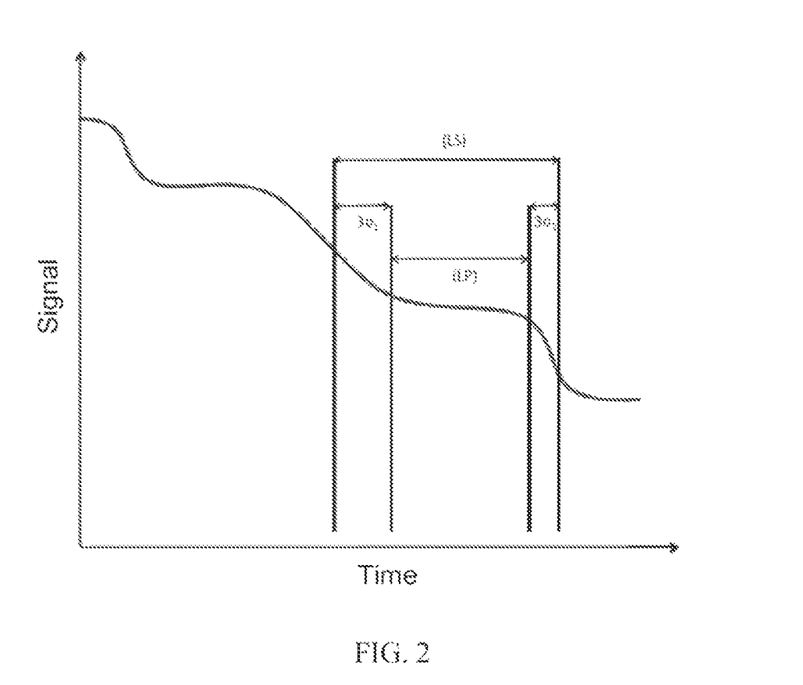

The separation by isotachophoresis of the charged species contained in the solutions is performed according to the principle schematically represented by steps i) to iii) of FIG. 1:

i) in the capillary, between the terminating electrolyte (T) and leading electrolyte (L), the solution to be analyzed, containing charged species such as the cations denoted A, B and C, is inserted. This is performed, for example, by filling the capillary with the leading electrolyte, injecting the solution to be analyzed through the inlet, of the capillary, then inserting the inlet of the capillary into the container containing the terminating electrolyte;

ii) a constant intensity (I) is established between the cathode (−) and the anode (+) so that the charged species separate according to increasing mobility by traveling over a separation length (Lsep) defined by the capillary inlet and a detector such as the conductometric sensor (CC) or the ICPMS spectrometer (not shown in FIG. 1);

iii) a measurement of the species is performed when they pass in front of the conductometric sensor, then an isotope measurement is performed when they are introduced into the ICPMS spectrometer.

The width of the signal obtained by isotachophoresis is theoretically considered to be representative of the quantity expressed as the mass of a charged species.

In practice, diffusion phenomena are observed.

The quality of the separation is evaluated by observing the cleanness of the transition between the different signals (a good separation between two charged species results in an abrupt transition between the respective signals of these species) and the possible presence of additional signals which corresponds to the mixture of two species having similar mobilities.

It may be determined numerically by calculating the resolution (Rs) according to the following formula:

$$RS=1-(3\sigma1+\sigma2)/LS,$$

in which, in accordance with FIG. 1, which can be transposed to detection by ICPMS spectrometry:

LS=width of a characteristic signal of a charged species;

LP=width of the section of the LS signal that is in the form of a plateau (i.e. in practice, the elution zone containing a 99% pure charged species);

$\sigma1$ or $\sigma2$=standard deviation on each border of LP, corresponding to a diffusion zone $\sigma1$ or $\sigma2$ in which a mixture in variable proportions is observed between the species of adjacent signals. Each diffusion zone is contained between a limit of the LP section and the inflection point immediately adjacent to the signal.

As indicated above, the calculation of the resolution (RS) on a band is facilitated and rationalized with respect to the calculation of the resolution on a peak, because it is performed on the basis of parameters (in particular LS) that are determined mathematically and not empirically.

A person skilled in the art may, in accordance with his or her general knowledge, improve the quality of the separation by modulating one or more of the following parameters:

the ratio between the volume of the solution to be analyzed and the volume of the separation section of the capillary;

the electro-osmotic flow;

the composition of the coating of the internal wall of the capillary, so as to limit, interactions with the species to be analyzed;

the duration of the separation, which must be long enough to reach equilibrium of the isotachophoresis in which the charged species are at a concentration equal to that of the leading electrolyte in specific contiguous zones. It is also possible to impose a strong current between the electrodes (typically between 1 μA and 50 μA according to the size of the capillary), while avoiding the Joule effect, in order to reach equilibrium faster.

The process conditions of the separation by isotachophoresis are indicated in Table A.

TABLE A

| ISOTACHOPHORESIS Analytical conditions | |
| --- | --- |
| reduction in the electro-osmotic flow (EOF) | yes |
| separation intensity | 1 µA |
| injected volume of solution to be analyzed | 1.4 µL |
| mean resolution per lanthanide | 0.7 |

To optimize the separation of the charged species, the capillary is subjected to specific adaptations.

1.1.1. Structure of the Capillary.

An association of two capillaries is produced so as to reduce the length of the injection zone while significantly increasing its volume. This is recommended when the solution to be analyzed has a volume that exceeds the volume of the capillary by at least 20%.

The capillary is comprised of a first capillary (internal diameter=150 µm, external diameter=375 µm, length=8 cm), which is force-fitted with a second capillary (internal diameter=30 µm, external diameter=375 µm, length=variable) using a Teflon connection with an internal, diameter of 325 µm. This connection enables the capillary to resist pressures of several bars without generating dead volume.

The first capillary defines an injection volume of 1.4 µL which is intended, to successively receive the leading electrolyte, the solution to be analyzed, and then the terminating electrolyte.

The second capillary can be broken down into a separation section and a so-called electrical section of 14 cm, consisting of the section located between the detection zone of the conductometric sensor and the outlet of the capillary opening into the nebulizer.

1.1.2. Pretreatment of the Capillary.

As is commonly used in capillary electrophoresis, the internal coating of the capillary comprised of silica is preferably pretreated with polyvinyl alcohol (PVA) to improve the separation of the charged species.

As the objective is to pre-treat a capillary of which a portion has an internal diameter of 30 µm, the concentration of the aqueous PVA solution is limited to 5% by mass so as to preserve a certain fluidity.

The capillary is first rinsed with a 1 M soda solution (2 bars, 30 minutes), then with a 1 M hydrochloric acid solution (2 bars, 30 minutes).

After drying under nitrogen (2 bars, 10 minutes), it is pretreated with a PVA solution acidified to pH 1 by adding hydrochloric acid, which is introduced at a pressure of 5 bars of nitrogen for 90 minutes.

The capillary is then emptied under a pressure of 2 bars and heated for 8 hours at 145° C. under nitrogen circulation at a pressure of 2 bars.

1.1.3. Contactless Conductometric Sensor.

While it is not essential for implementing the measurement method of the invention, the capillary electrophoresis device contains a contactless conductometric sensor (of the C4D type: "Tracedec" model, marketed by the Innovative Sensor Technologies GmbH company) in order to evaluate the efficacy of the separation of the charged species upstream of the detection by the ICPMS spectrometer.

Such a conductometric sensor detects a species owing to the change in conductivity that it produces during its migration through the capillary. It does not have any contact with the solution to be analyzed or the electrolytes, and therefore does not have any influence on the separation.

In practice, the conductometric sensor is placed in the thermostatically controlled cassette along a portion of the capillary and at a short distance from the nebulizer. By moving the sensor along the capillary, a position at which the separation occurs under sufficient conditions generally appears. In this case, she quality of the separation no longer changes when the sensor is placed at a distance of 14 cm from the cathode end of the capillary.

The process conditions of the conductometric sensor are indicated in Table B.

TABLE B

| CONTACTLESS CONDUCTOMETRIC SENSOR | |
| --- | --- |
| frequency | 2 * HIGH |
| voltage | −18 dB |
| gain | 100% |
| offset | 020 |
| type | CE |
| sensor | HS |
| frequency of acquisition | 5.47 Hz |
| filter | FAST |

1.2. Nebulizer.

When the direct coupling is performed between a capillary electrophoresis device and an ICPMS spectrometer, it is preferable to compensate for the difference in flow rate between the outlet of the capillary (1 to 100 nL/min) and the inlet of the ICPMS spectrometer (20 to 1000 µL/min) while closing the electrical circuit at the outlet of the capillary.

For this, the chosen interface between the capillary electrophoresis device and the ICPMS spectrometer is a nebulizer ("Mira Mist CE" model, marketed by the Burgener company). This nebulizer enables a homogeneous aerosol to form, without the effect of suction of the contents of the capillary, which would impair the separation by forming a parasitic flow and by draining the capillary. The nebulization is produced by an argon flow.

The position of the capillary inside the body of the nebulizer is optimized in order to improve the sensitivity of the transient signals. The outlet of the capillary is, in this case, set back 1 mm from the inlet of the nebulizer.

According to the manufacturer's recommendations, this nebulizer is connected to a T-joint comprising a first inlet receiving the capillary, a second inlet receiving the cathode through which a coaxial conduit passes, carrying a make-up solution, and an outlet opening into a nebulization chamber connected to the ICPMS spectrometer.

The nebulizer opens into a nebulization chamber that is a linear Teflon micro-chamber offering a reduced aerosol transfer rate and a reduced residence time.

The make-up solution makes it possible to close, the electrical circuit and adapt, the flow rate of the capillary electrophoresis device to the working flow rate of the ICPMS spectrometer. It is stored in a 10 ml polypropylene syringe. Its flow rate, generally between 0.005 and 1 mL/min, is set at 10 µL/min (by a syringe pump marketed by the Harvard Apparatus company).

The make-up solution has the composition of the leading electrolyte, making it possible to preserve the equilibrium of the separation by providing the system, as the case may be, with the complexing agent throughout the measurement.

1.3. ICPMS Spectrometer.

Two ICPMS spectrometers differing by their mass spectrometer are used in the isotope measurements: a quadripolar ICPMS spectrometer (X7 model, series 2, Thermo Electron marketed by the Thermo Fisher Scientific company) and a multi-collection ICPMS spectrometer (IsoProbe model with magnetic sector and multi-collector, marketed by the CV Instruments company), which make it possible respectively to perform an isotope measurement with precision on the order of several hundredths and thousandths.

1.3.1. Quadripolar ICPMS Spectrometer.

The detection by quadripolar ICPMS (ICP-QMS) is first optimized in the absence of separation by isotachophoresis.

For this, an Nd test solution is injected up to the nebulizer by applying a constant pressure of 30 mbars on the capillary filled with the leading electrolyte. The positioning adjustments of the plasma torch, the gas flow rates and the ionic optics are then adjusted to obtain an optimum signal at mass 142 ($^{142}$Nd+).

The stability of the signal is controlled by calculating the ratio of the standard deviations of the measurements relative to the mean values as a percent (RSD) on a series of 10 successive measurements. The ratio between the signals $^{142}$NdO$^+$/$^{142}$Nd$^+$ (%) makes it possible to directly determine the oxide content. The RSDs obtained typically vary between 1% and 10% for the stability of the signal. The oxide content is typically less than 3%.

After optimization, the ICP-QMS spectrometer is implemented according to the process conditions indicated in Table C.

TABLE C

| ICP-QMS (quadripolar) | |
|---|---|
| radiofrequency power of the plasma | 1100 W |
| nebulization gas flow rate | 0.7-0.8 L/min |
| auxiliary gas flow rate | 0.9 L/min |
| cooling gas flow rate | 15 L/min |
| peak width at 10% of the height | 0.82 atomic mass units (u) |
| measurement mode | peak hopping |
| integration time per measurement | 50 ms |

1.3.2. Multi-Collection ICPMS Spectrometer

The ICPMS Multi-Collection Spectrometer (ICP-MC-MS) is a single-focusing magnetic sector instrument (IsoProbe model marketed by the GV Instruments company).

It is equipped with an ICP source, a collision-reaction cell, a magnetic sector and a multi-collection system, as well as a Daly electrode implanted in the axial position. A platinum guard electrode is inserted between the torch and the coil in order to increase the sensitivity of the measurements and suppress the secondary capacitive discharge effects.

The multi-collection system of the ICP-FC-MS comprises nine Faraday cages (L2 located at the left of the axial cage AX, and H1 to P7 located at the right) making it possible to simultaneously measure the different isotope signals.

They are positioned by injecting a standard solution containing the isotopes of interest. The gain parameters of the Faraday cages are calibrated just before the measurements in order to obtain reproducibility of the electrical gains better than 20 ppm/day.

The intensity of the ion beam is optimized by adjusting the position of the torch, the gas flow rates, the ionic optics and the adjustment parameters of the magnetic sector.

The measurement is performed according to a series of 2 blocks of 10 measurements or cycles with an integration time of 10 seconds per cycle.

The main process conditions of the ICP-MC-MS for the measurement of solution 3 (Nd, Sm) are indicated in Table D. Because of the limited number of Faraday cages, only the isotopes of mass 142 to 150 are detected simultaneously.

TABLE D

| ICP-MC-MS (Multi-collection) | | |
|---|---|---|
| radiofrequency power of the plasma | | 1350 W |
| nebulization gas flow rate | | 0.78 L/min |
| auxiliary gas flow rate | | 1.2 L/min |
| cooling gas flow rate | | 14 L/min |
| integration time per measurement | | 300 ms |
| number of measurements per value | | 100 ms |
| attribution of collectors | Nd | Sm |
| L2 | $^{142}$Nd | |
| Ax | $^{143}$Nd | |
| H1 | $^{144}$Nd | $^{144}$Sm |
| H2 | $^{145}$Nd | |
| H3 | $^{146}$Nd | |
| H4 | | $^{147}$Sm |
| H5 | $^{148}$Nd | $^{148}$Sm |
| H6 | | $^{149}$Sm |
| H7 | $^{150}$Nd | $^{150}$Sm |

2. Preparation of the Electrolytes and the Solutions to Be Analyzed.

2.1. Electrolytes.

The electrolytes are preferably free of compounds with a low ionization potential such as sodium or inorganic salts that, in ICPMS spectrometry and at high concentrations, can produce matrix effects and obstruct the extraction cones.

The leading electrolyte is comprised of acetic acid ($10.10^{-3}$ mol/L) to which 2-hydroxy-2-methylbutyric acid (HMBA, $14.10^{-3}$ mol/L) is added as a complexing agent. It has a pH of 4.5 after adjustment by adding NH$^{4+}$ which constitutes the cation with mobility greater than that of the lanthanides to be analyzed. As the deprotonated free form of the complexing agent is anionic, it passes through the capillary, continuously migrating toward the anode during the separation by isotachophoresis.

The terminating electrolyte is comprised of acetic acid ($15.10^{-3}$ mol/L, pH=3.3). The very mobile protons of the terminating electrolyte are partially consumed by the deprotonated form of the complexing agent.

2.2. Solutions to be Analyzed.

The three solutions to be analyzed are prepared from commercial lanthanide solutions (standard single-element solutions marketed by the SPEX Certiprep company).

These commercial solutions contain a high concentration of nitric acid (5%). They are subjected to a preparatory treatment in which they are dried twice at a temperature of 90° C., then returned to an equivalent volume with ultrapure water coming from an Elga UHQII system (marketed by Veolia Water).

After dilution, solutions 1 to 3 are obtained, the composition of which is described in the corresponding analyses.

3. Analysis of Solutions.

3.1. Analysis of Solution 1 (Four Lanthanides at the Same Concentration).

A solution 1 is prepared, comprising four lanthanides (Nd, Sm, Eu and Gd) of which Table E indicates the isotopic composition according to the natural abundance of each isotope and the potential isobaric interferences between the lanthanides, or between the lanthanides and their oxides.

The concentration of each lanthanide, all isotopes combined, is 3.6 ng/μL.

TABLE E

| Mass (u) | Nd | Sm | Eu | Gd |
|---|---|---|---|---|
| 142 | 142 (27.16%) | | | |
| 143 | 143 (12.18%) | | | |
| 144 | 144 (23.83%) | 144 (3.07%) | | |
| 145 | 145 (8.30%) | | | |
| 146 | 146 (17.17%) | | | |
| 147 | | 147 (14.99%) | | |
| 148 | 148 (5.74%) | 148 (11.24%) | | |
| 149 | | 149 (13.81%) | | |
| 150 | 150 (5.62%) | 150 (7.37%) | | |
| 151 | | | 151 (47.81%) | |
| 152 | | 152 (26.74%) | | 152 (0.20%) |
| 153 | | | 153 (52.19%) | |
| 154 | | 154 (22.752%) | | 154 (2.18%) |
| 155 | | | | 155 (14.79%) |
| 156 | | | | 156 (20.46%) |
| 157 | | | | 157 (15.65%) |
| 158 | 142 + O16 | | | 158 (24.83%) |
| 159 | | | | |
| 160 | 144 + O16 | 144 + O16 | | 160 (21.86%) |

Solution 1 is subjected to separation by isotachophoresis in which the second capillary has a total length of 94 cm comprising a separation section of 80 cm up to the conductometric sensor located upstream of the ICP-QMS spectrometer.

Figure 3:
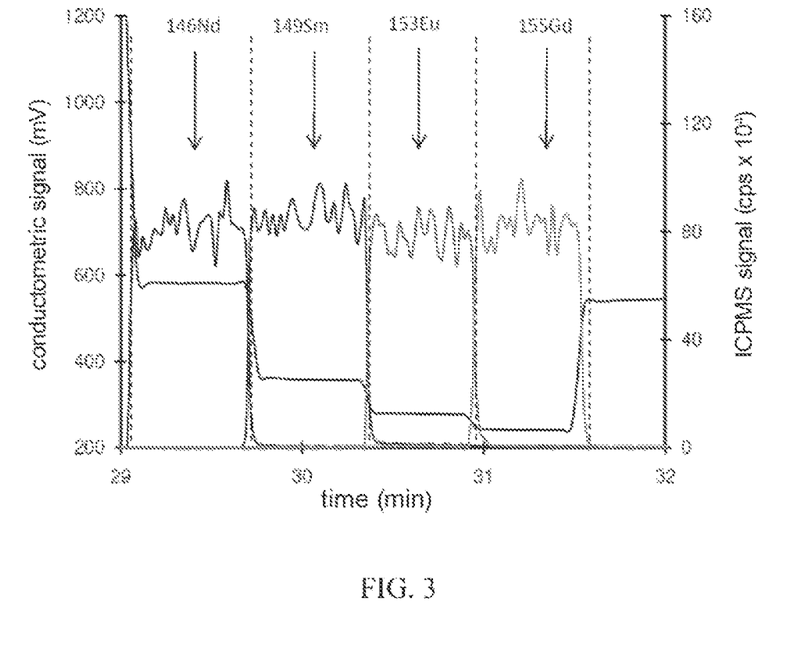
FIGS. 3 and 4 show the signal obtained by conductometric detection and detection by ICPMS, after separation by isotachophoresis of the lanthanides Nd, Sm, Eu and Gd.

The results are shown in FIG. 3 in which the zones specific to each lanthanide are defined by vertical bars of dotted lines, and appear in the form of a band.

FIG. 3 superimposes the signals obtained in conductometry (steps) and ICPMS (bands). The difference in the separation lengths between these two detectors generates a detection delay. To simplify the comparison of the isotachopherograms obtained, the signals of the ICPMS are artificially translated over time.

The detection by ICPMS makes it possible to distinguish different isotopes of the same lanthanide in solution 1. However, only the bands specific to an isotope of each lanthanide not having an isobaric interference ($^{146}$Nd, $^{149}$Sm, $^{153}$Eu, $^{155}$Gd) are shown in FIG. 3. The amplitude of each band is corrected according to the natural isotopic abundance of each isotope (for example, the amplitude of the signal of $^{153}$Eu is corrected by a factor 100/52.19). The width of the band is proportional to the concentration of the lanthanide considered (3.6 ng/μL).

Owing to the selectivity of the detection using an ICPMS spectrometer, the bands specific to each lanthanide appear to be clearly separated.

This makes it possible to easily quantify the quality of the separation for a charged species by calculating the resolution (Rs) on the basis of the parameter LB for which the parameter LP can possibly be substituted.

Such a result cannot be obtained using conductometric detection in which the amplitude of the signal corresponds to the sum of the individual conductivities of all of the isotopes of a detected charged species, not enabling these isotopes to be directly identified or precisely quantified.

Moreover, as indicated above, when a to current intensity is applied during the isotachophoresis, its duration is increased, without it affecting the quality of the separation.

Owing to the extreme sensitivity and the extent of the linearity of the signal over several orders of magnitude of the detection by ICPMS spectrometer, this makes it possible to enlarge the ICPMS detection band, and therefore to further increase the stability and precision of the isotope measurement on the basis of this band.

3.2. Analysis of Solution 2 (4 Lanthanides of Different Concentrations with Charsed Matrix)

As a complementary experiment, solution 2 is prepared by adding to solution 1 different elements in ionic form according to the proportions indicated in Table F, in order to simulate a real sample comprising a charged matrix such as that of a reconstituted UOx-type nuclear fuel. The sum of the elements represents a total concentration of 280 ppm.

Solution 2 is analyzed under the same conditions as solution 1, except that the isotopes measured are partially different ($^{146}$Nd, $^{149}$Sm, $^{151}$Eu, $^{157}$Gd).

Figure 4:
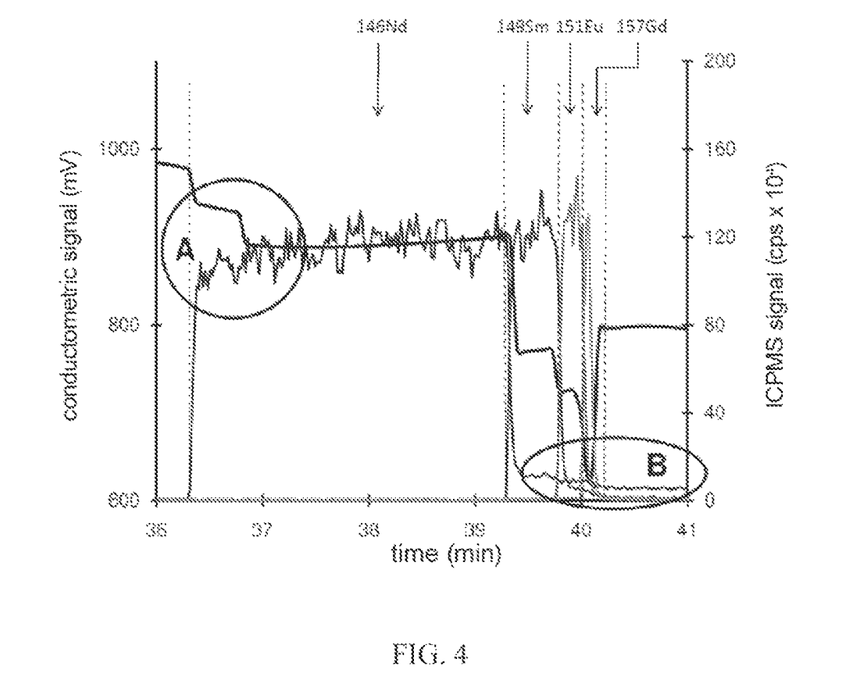

The results are shown in FIG. 4, in which a translation of the ICPMS spectrum is performed as above.

They show that the presence of this matrix does not affect the detection by ICPMS spectrometer, while the conductometric detection creates artifacts (reference A) and does not enable the species in low concentrations such as $^{155}$Gd (reference B) to be detected.

TABLE F

| element | mass abundance |
|---|---|
| Se | 0.15% |
| Rb | 0.91% |
| Sr | 2.11% |
| Y | 1.18% |
| Zr | 9.85% |
| Mo | 9.72% |
| Ru | 7.17% |
| Rh | 1.07% |
| Pd | 5.25% |
| Ag | 0.23% |
| Cd | 0.41% |
| In | 0.00% |
| Sn | 0.24% |
| Sb | 0.06% |
| Cs | 7.01% |
| Ba | 5.10% |
| La | 3.42% |
| Ce | 6.82% |
| Pr | 3.15% |
| Nd | 11.60% |
| Sm | 2.14% |
| Eu | 0.51% |
| Gd | 0.68% |
| Tb | 0.01% |
| Dy | 0.01% |
| Ho | 0.00% |

3.3. Analysis of Solution 3 (Mixture of Nd and Sm).

A solution 3 is prepared by mixing an equivalent volume of a solution of 1000 mg/g of Nd and a solution of 10000 mg/g of Sm, which comprise the different isotopes of these lanthanides according to their natural isotopic abundance.

After performing the preparatory treatment described above, solution 3 is degassed under ultrasound, filtered on cellulose (0.2 μm), then diluted so that each of the lanthanides Nd and Sm is present at a concentration of 6250 μg/g.

A volume of 80 mL of solution 3 corresponding to a quantity of 5 ng per lanthanide is injected into a capillary electrophoresis device consisting of a fluidic microsystem (CE Chip T8050 model marketed by the Micronit company, comprising channels 50 μm wide and 20 μm deep and a modified distance between the two T of 80 mm instead of the standard 0.1 mm) connected by direct coupling to the ICPMS-MC spectrometer via the nebulizer.

The capillary contained in the fluidic micros stem has a total length of 100 cm, which corresponds to the separation length, because, as the fluidic microsystem does not comprise a conduct sensor, the separation continues up to the outlet end of the capillary that opens into the nebulizer.

After separation of Sm and Nd by isotachophoresis, a measurement is performed on certain isotopes of these lanthanides ($^{142}$Nd, $^{143}$Nd, $^{144}$Nd and $^{144}$Sm, $^{145}$Nd, $^{146}$Nd, $^{147}$Sm, $^{148}$Nd and $^{148}$Sm, $^{149}$Sm, $^{150}$Nd and $^{150}$Sm).

Figure 5:
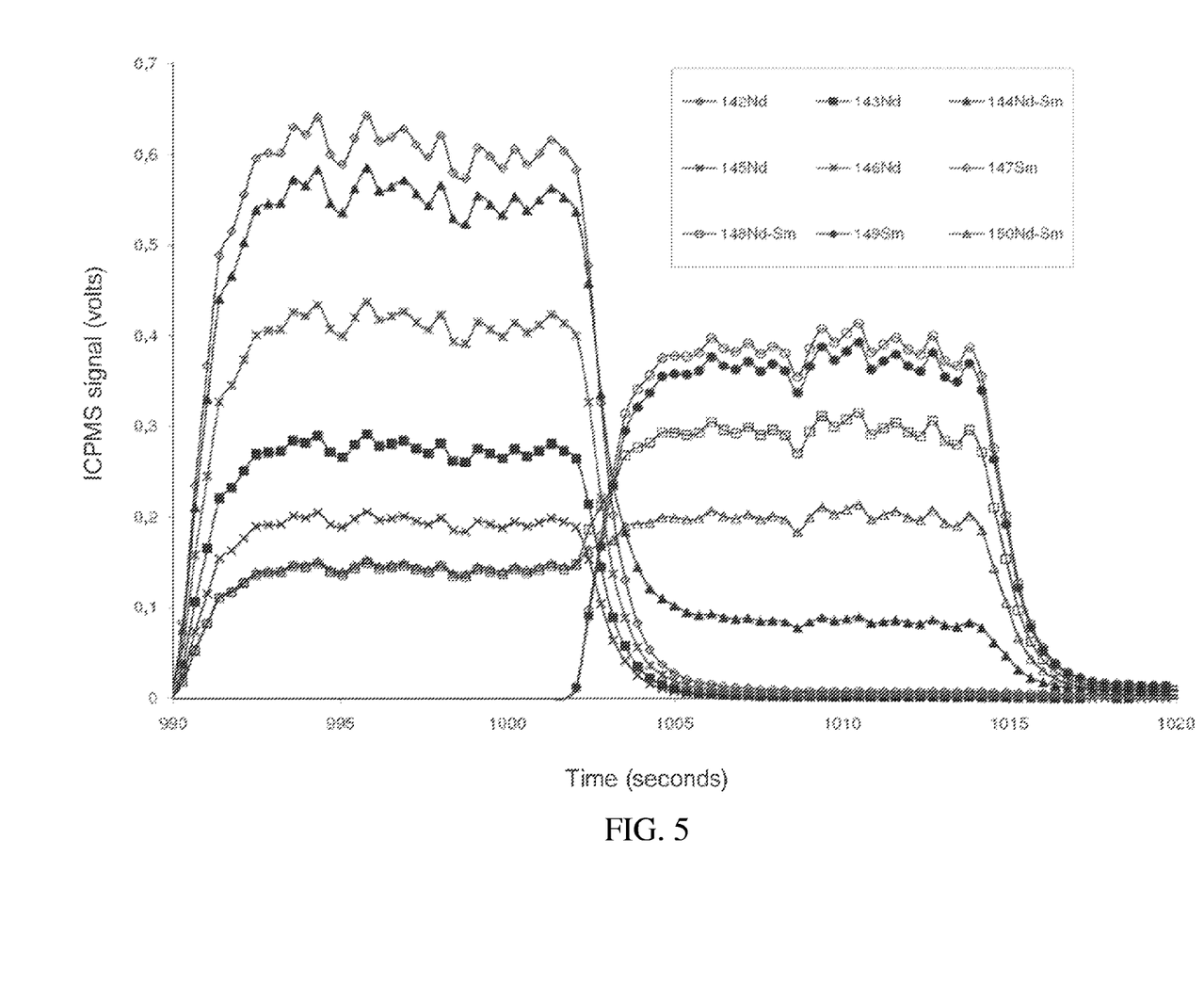
FIG. 5 shows the signal obtained by ICPMS detection of isotopes of the lanthanides Nd and Sm after separation of these elements by isotachophoresis.

The results obtained are reproduced in FIG. 5, in which the diffusion zones and the bands specific to the isotopes of the Nd (between 990 and 1002 seconds) and the Sm (between 1006 and 1014 seconds) can be fully seen. The amplitude of each band is proportional to the natural isotopic abundance of the isotope measured.

This separation of Nd and Sm makes it possible to resolve the isobaric interferences (masses 144, 148 and 150) and thus precisely obtain the isotope measurement.

Numerous ICPMS measurement points are obtained in spite of the small volume injected.

The reproducibility obtained is several thousandths, which is comparable to the results that can be obtained in an isotope measurement by indirect coupling.

The invention claimed is:

1. Method for isotope measurement of at least one isotope of at least one charged species contained in a solution to be analyzed said solution containing at least two charged species, in which said charged species are selected independently from the group consisting of inorganic cations, inorganic anions, and charged organometallic compounds, at least two of said species having at least one isobaric interference so that the difference in atomic mass between said species is between 0.001 and 0.9 atomic mass units, the method comprising the following consecutive steps:
   a) providing a capillary electrophoresis device comprising a capillary having an inlet and an outlet and, in the capillary, inserting contiguously the solution to be analyzed between a terminating electrolyte and a leading electrolyte that, respectively, are placed after the inlet and before the outlet of the capillary and contain ions of the same charge but with mobility inferior and superior to those of said species;
   b) separating said species by performing isotachophoresis with the capillary electrophoresis device, then;
   c) in the continuity of the preceding step, performing an isotope measurement of at least one said species, wherein said species is detected in the form of a substantially constant amplitude signal by using an inductively coupled plasma mass spectrometer (ICPMS) connected by direct coupling with the capillary electrophoresis device.

2. Method for isotope measurement according to claim 1, wherein the isotachophoresis is performed by applying a voltage that results in a current with an intensity of between 0.1 µA and 10 µA.

3. Method for isotope measurement according to claim 1, wherein the isotope measurement comprises an isotope dilution.

4. Method for isotope measurement according to claim 1, wherein the isotope measurement comprises determining an isotopic abundance for each of a plurality of the different isotopes of the same species.

5. Method for isotope measurement according to claim 1, wherein the leading and/or terminating electrolyte is an aqueous solution of a compound comprising the elements carbon, hydrogen and oxygen.

6. Method for isotope measurement according to claim 1, wherein the terminating electrolyte is a zwitterionic compound.

7. Method for isotope measurement according to claim 1, wherein the capillary electrophoresis device is entirely or partially implanted on a fluidic microsystem.

8. Method for isotope measurement according to claim 1, wherein the capillary electrophoresis device and the ICPMS spectrometer are connected by direct coupling via a system enabling drops to be generated.

9. Method for isotope measurement according to claim 1, wherein the ICPMS spectrometer is of a multi-collection type.

10. Method for isotope measurement according to claim 1, wherein said species are transition, alkaline or alkaline earth metals, lanthanides and/or actinides.

11. The method according to claim 1, wherein the isotope measurement comprises determining the presence or absence of at least one isotope of at least one charged species.

12. The method according to claim 1, wherein the isotope measurement comprises determining the concentration in said solution of at least one isotope of at least one charged species.

13. Method for isotope measurement according to claim 1, wherein the capillary contains a complexing agent intended to form a complex with all or some of said species during the isotachophoresis.

14. Method for isotope measurement according to claim 13, wherein the complexing agent is chosen from 2-hydroxy-2-methyl butyric acid (HMBA), hydroxyisobutyric acid (HIBA), ethylenediaminetetraacetic acid (EDTA), pyridine-2,6-dicarboxylic acid (PDCA), lactic acid, tartric acid, oxalic acid, maleic acid, isobutyric acid or mixtures thereof.

15. Method for isotope measurement according to claim 13, wherein the complexing agent is contained in the leading electrolyte.

16. Method for isotope measurement according to claim 13, wherein an assisting agent is added to the complexing agent.

17. Method for isotope measurement according to claim 16, wherein the assisting agent is chosen from diglycolic acid, malonic acid, tartric acid, maleic acid, formic acid, citric acid, acetic acid, or mixtures thereof.

18. Method for isotope measurement according to claim 16, wherein the assisting agent is contained in the leading electrolyte.

* * * * *